United States Patent [19]

Myers, Jr. et al.

[11] 4,331,648

[45] May 25, 1982

[54] N-ACETYL-CYSTEINE PROTECTS AGAINST CARDIAC DAMAGE FROM SUBSEQUENTLY-ADMINISTERED CARDIO-TOXIC ANTHRA-CYCLINE IN CANCER THERAPY

[75] Inventors: Charles E. Myers, Jr., Rockville, Md.; James H. Doroshow, Upland, Calif.; Gershon Y. Locker, Chicago, Ill.

[73] Assignee: The United States of America as represented by the Secretary of the Department of Health and Human Services, Washington, D.C.

[21] Appl. No.: 190,064

[22] Filed: Sep. 23, 1980

Related U.S. Application Data

[63] Continuation-in-part of Ser. No. 100,496, Dec. 5, 1979, abandoned, which is a continuation of Ser. No. 24,246, Mar. 27, 1979, abandoned.

[51] Int. Cl.³ .................... A61K 31/70; A61K 31/71
[52] U.S. Cl. .................... 424/10; 424/180; 424/181
[58] Field of Search .................... 424/10

[56] References Cited

U.S. PATENT DOCUMENTS 4,267,163  5/1981  DeFelice ..................... 424/180

OTHER PUBLICATIONS

Chemical Abstracts, 79: 142981a, (1973).
Chemical Abstracts, 92: 52213r, (1980).

*Primary Examiner*—Jerome D. Goldberg
*Attorney, Agent, or Firm*—Holman & Stern

[57] ABSTRACT

The cardiac damage, occurring after treatment with an anthracycline, such as adriamycin, is prevented when N-acetyl-cysteine is orally administered about one hour prior to the treatment with the anthracycline.

10 Claims, No Drawings

N-ACETYL-CYSTEINE PROTECTS AGAINST CARDIAC DAMAGE FROM SUBSEQUENTLY-ADMINISTERED CARDIO-TOXIC ANTHRA-CYCLINE IN CANCER THERAPY

This is a continuation-in-part of application Ser. No. 100,496 filed Dec. 5, 1979, now abandoned, which is a continuation of application Ser. No. 24,246 filed Mar. 27, 1979, now abandoned.

This invention relates to N-acetyl-cysteine having the formula

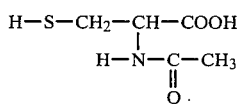

and has as its object the use of this compound to block cardiac damage resulting from the use of anthracyclines, notably adriamycin, in cancer therapy.

The anthracyclines have the general formula

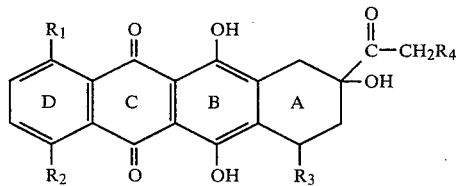

and their essential structure is based on the anthraquinone ring which characteristically has a quinone functionality on the C ring and a hydroquinone function on the B ring. In addition, a hexose sugar is commonly attached via glycosidic linkage at $R_3$. Daunosamine is the most common sugar to be found at $R_3$. $R_1$, $R_2$, and $R_4$ can vary widely, and for the two anthracyclines presently in clinical use, namely, doxorubicin (known as adriamycin) and duanomycin, $R_1$, $R_2$, and $R_4$ are H, $OCH_3$, OH, and H,$OCH_3$, and H, respectively, and $R_3$ is daunosamine.

The anthracyclines are members of the Rhodomycin group of antibiotics produced by Streptomyces (Di Marco, A. et al. *Nature* 201:706, 1964). The anthracyclines are of interest because a number of them show considerable activity against a wide range of human and animal tumors. Two members of this group, daunomycin and doxorubicin (adriamycin), are in widespread use in this country as anticancer agents (Carter, S. K. *JNCI* 55: 1265, 1975). Other anthracyclines, including: (a) rubidazone, the benzoyl hydrazone derivative of daunorubicin; (b) carminomycin, which differs structurally from adriamycin by the substitution of a hydroxyl for a methoxy group on $R_2$ and the absence of the hydroxyl group on $R_4$; and (c) 7-con-O-methylnogarol; are also known to be useful as anticancer agents. However, the clinical use of these drugs is impaired because they cause cardiac damage in both man and animals (Lefrak, E. A. et al. *Cancer Chemother. Rep.* Part 3, 6: 203, 1975; Doroshow et al. *Cancer Treat. Rep.*, in press, 1979). See also McGovren, J. P. et al., *Cancer Research*, 39, 4849–4855, Dec. 1979; Merski, J. A. et al., *Cancer Research*, 39, 1239–1244, April 1979; and Benjamin, R. S., *Cancer Research*, 37, 4623–4628, Dec. 1977.

Prior Art

Initial work in this laboratory has indicated that free radical scavengers, such as Vitamin E, were effective in lessening the cardiac damage of one of the anthracyclines, namely, doxorubicin (adriamycin), without impairing its antitumor effectiveness (*Science* 197: 165, 1977). Subsequent work in this laboratory has indicated, however, a number of limitations in the use of Vitamin E for this purpose. It is ineffective orally and so must be given parenterally. However, no satisfactory parenteral formulation exists for human use. For these reasons, we began to search for a non-toxic, water-soluble radical scavenger, well-absorbed orally, and as effective or more effective than Vitamin E.

In general, according to the invention, the cardiac damage usually resulting following the administration of an anthracycline (e.g., adriamycin) is greatly reduced or effectively prevented by the administration of N-acetylcysteine, preferably orally, prior to the administration of the anthracycline, especially if the N-acetyl-cysteine is administered about one hour prior to the administration of the anthracycline.

The properties which N-acetyl-cysteine exhibits that favor its use as an agent to prevent anthracycline-induced cardiac damage are (1) It is well-tolerated and absorbed orally in man and animals; (2) It is more effective than Vitamin E in lessening the cardiac damage associated with anthracycline exposure; and (3) It does not impair the antitumor effectiveness of the anthracyclines. The documentation of these points follows:

1. Oral Absorption in Man and Animals

Extensive previously published work dealing with the action of N-acetyl-cysteine as a mucolytic agent (e.g., U.S. Pat. No. 3,184,505 to T. A. Martin et al) indicate that it is rapidly absorbed orally in man and animals. From species to species, there are significant differences in the rate at which N-acetyl-cysteine is removed from the bloodstream. In man, the levels rise rapidly to a peak and then decline slowly over many hours (Rodenstein, D., *Clinical Pharmacokinetics* 3: 247, 1978). In rodents, for example, the blood levels rise rapidly to a peak and then fall as rapidly to low levels within 1-2 hours (Sheffner, A. L., *Biochem. Pharm.* 15: 1523, 1966).

2. Effectiveness in Preventing Cardiac Damage

We have studied the effectiveness of N-acetyl-cysteine in preventing cardiac damage in mice, a species which is markedly sensitive to the cardiac damage. The $CDF_1$ strain of mice used in our work developed widespread severe damage to the heart within 4 days after a single dose of doxorubicin (adriamycin) as judged by electron microscopy (*Science* 197: 165, 1977).

In the present invention, four groups of mice were studied: (1) Those which received 2 gm of N-acetyl-cysteine per kg of body weight of mouse (2 g/kg) orally 1 hour prior to 15 mg of doxorubicin (adriamycin) per kg of body weight of mouse (15 mg/kg) i.p. (intraperitoneally); (2) Those which received 2 gm/kg N-acetyl-cysteine orally alone: (3) Those which received 15 mg/kg doxorubicin (adriamycin) i.p. alone; and (4) Those which received saline i.p. alone. The animals were sacrificed on the fourth day after drug administration and their hearts processed for electron microscopy. The group which received doxorubicin (adriamycin) exhibited the expected widespread damage. The group which received both N-acetyl-cysteine and doxorubicin (adriamycin) exhibited no detectable damage and, in fact, was not distinguishable from animals which received saline alone. In a similar experiment, Vitamin E exhibited only partial protection.

When the dose of N-acetyl-cysteine used was varied between 500 mg/kg and 2 gm/kg but the doxorubicin (adriamycin) dose held constant, partial protection was observed at 750 mg/kg but full protection did not occur until a dose of 2 gm/kg was attained. The latter dose corresponds to a dose of 5 g per square meter of the surface area of a man (i.e. 5 g/m$^2$) and such a dose has been well-tolerated in man on a daily basis for time periods in excess of one year.

Because of the rapid clearance of N-acetyl-cysteine from the bloodstream seen in rodents, we studied the effect of timing of the N-acetyl-cysteine dose on the protective effect of this compound on anthracycline toxicity. Again, CDF$_1$ mice were used and 15 mg/kg of doxorubicin (adriamycin) was administered i.p. The dose of N-acetyl-cysteine used was 2 gm/kg and this was administered 3 hours before, 1 hour before, 30 minutes before, simultaneous with, 1 hour after, or 2 hours after the doxorubicin (adriamycin) was administered. Pretreatment with N-acetyl-cysteine one hour prior to doxorubicin (adriamycin) was clearly the most effective with all other schedules exhibiting less than 60% of the protection observed with the 1 hour pretreatment schedule.

3. Anti-Tumor Effectiveness

The impact of N-acetyl-cysteine on antitumor effectiveness of the anthracyclines was tested again in CDF$_1$ mice. The tumor line selected for study was P388 ascites tumor, noted as one of the most sensitive of the murine tumors to doxorubicin (adriamycin). Four groups of CDF$_1$ mice were treated as follows:

(1) One group received 1 million P388 ascites tumor cells i.p. only; (2) A second group received 1 million P388 ascites tumor cells i.p. plus 2 gm of N-acetyl-cysteine i.p. 24 hours after tumor implantation; (3) a third group received 1 million P388 ascites tumor cells i.p. plus 10 mg/kg of doxorubicin i.p. 24 hours later; and (4) a fourth group received 1 million P388 ascites tumor cells i.p. plus 2 gm of N-acetyl-cysteine i.p. followed in 24 hours by 10 mg/kg of doxorubicin i.p. Groups 1 and 2 both survived a median of 8 days following tumor implantation. Groups 3 and 4 both survived a median of 13 days post implantation. These experiments demonstrate that N-acetyl-cysteine does not in and of itself possess antitumor properties and it does not interfere with doxorubicin's ability to treat the sensitive P388 ascites tumor.

Effect of N-acetyl-cysteine on Doxorubicin Pharmacokinetics

The ability of N-acetyl-cysteine to protect from doxorubicin damage might occur because N-acetyl-cysteine caused either more rapid clearance of doxorubicin from the blood or prevented its penetration into heart muscle. In either case, one would expect low cardiac tissue levels of doxorubicin. To test this, we directly measured the concentration of doxorubicin in mouse hearts after doxorubicin alone or doxorubicin with N-acetyl-cysteine pretreatment. In the animals treated with doxorubicin alone, the drug concentration peaked at 3 hours and gradually fell to low levels by 48 hours. Animals receiving doxorubicin plus N-acetyl-cysteine pretreatment exhibited a similar rise and fall not different statistically from the animals which received N-acetyl-cysteine alone. The data upon which these results are based are summarized in the following table:

| EFFECT OF N-ACETYL-CYSTEINE ON CARDIAC DOXORUBICIN LEVELS | | |
|---|---|---|
| Time | Doxorubicin Alone | Doxorubicin Plus N-acetyl-cysteine |
| ½ hour | 2,200$^a$ | 2,300 |
| 1 hour | 2,390 | 2,400 |
| 3 hour | 2,800 | 2,750 |
| 18 hour | 1,510 | 1,450 |
| 24 hour | 1,540 | 1,525 |
| 48 hour | 785 | 850 |

$^a$Nanograms per gram cardiac wet weight.

Thus, the protection of cardiac tissue is not the result of lessened delivery to or entrance of doxorubicin into cardiac tissue.

Formulation

N-acetyl-cysteine has an unpleasant odor and taste. We have found that oil of peppermint masks the odor and cola soda masks the taste. When used together, this compound is much more pleasant to take orally.

SUMMARY

N-acetyl-cysteine protects against the cardiac damage of the anthracyclines without affecting either tumor response or delivery of the drug to tissue sites such as cardiac tissue. It has the advantage of being well-absorbed, effective orally, and tolerated in man and animals.

We claim:

1. A method of protecting a cancer patient being treated for antitumor purposes with a therapeutically acceptable and effective amount of a cardio-toxic anthracycline drug against usually-ensuing cardiac damage without affecting tumor response or delivery of the drug to cardiac tissue sites, comprising orally administering a range of from 750 mg to 2 grams per kg of N-acetyl-cysteine to a patient undergoing therapy with a cardio-toxic anthracycline drug.

2. The method of claim 1 wherein the anthracycline drug is adriamycin.

3. The method of claim 1 wherein the anthracycline drug is daunomycin.

4. The method of claim 1 wherein the dosage of N-acetyl-cysteine administered is 2 grams of N-acetyl-cysteine per kilogram of body weight.

5. The method of claim 1 wherein the dosage of N-acetyl-cysteine administered is 5 grams of N-acetyl-cysteine per square meter of the surface area of the human body.

6. The method of claim 1 wherein the N-acetyl-cysteine is administered about 1 hour prior to the administration of the anthracycline.

7. The method of claim 1 wherein the anthracycline is adriamycin, the dosage of N-acetyl-cysteine administered is 5 grams of N-acetyl-cysteine per square meter of the surface area of the human body, and the N-acetyl-cysteine is administered about 1 hour prior to the administration of the adriamycin.

8. The method of claim 1 wherein the anthracycline drug is rubidazone.

9. The method of claim 1 wherein the anthracycline drug is carminomycin.

10. The method of claim 1 wherein the anthracycline drug is 7-con-O-methylnogarol.

* * * * *